United States Patent [19]

Salazar-Grueso

[11] Patent Number: 5,229,394
[45] Date of Patent: Jul. 20, 1993

[54] METHOD FOR TREATMENT OF AMYOTROPHIC LATERAL SCLEROSIS COMPRISING ADMINISTRATION OF DMP

[75] Inventor: Edgar F. Salazar-Grueso, Chicago, Ill.

[73] Assignee: Arch Development Corporation, Chicago, Ill.

[21] Appl. No.: 560,084

[22] Filed: Jul. 30, 1990

[51] Int. Cl.⁵ .............................................. A61K 31/44
[52] U.S. Cl. ..................... 514/289; 514/879
[58] Field of Search ..................... 514/289, 879

[56] References Cited

U.S. PATENT DOCUMENTS 4,806,543  2/1989  Choi ..................... 514/464
4,888,347  12/1989  Woodruff et al. ..................... 514/289

OTHER PUBLICATIONS

Rowland, "Human Motor Neuron Diseases," *Advances in Neurology*, vol. 36, pp. 5-6 (1990).
Walker, S. O. et al. (1989), *Clinical Neuropharmacology*, vol. 12, pp. 322-330, 1989.
Gillberg, P. et al. Acta Neurol. Scand. 72:299-306 (1985).
Spencer, P. S. et al. Science 237:517-521 (1987).

*Primary Examiner*—Glennon H. Hollrah
*Assistant Examiner*—Gary E. Hollinden
*Attorney, Agent, or Firm*—Arnold, White & Durkee

[57] ABSTRACT

A method for treating ALS (Amyotrophic Lateral Sclerosis) is disclosed. The inventive method comprises the administration of controlled dosages of dextromethorphan in therapeutically effective amounts in a pharmaceutically acceptable vehicle Dextromethorphan (DMP) is a dimethylaminomethyl-substituted phenol, a sigma receptor antagonist known also as d-3-methoxy-N methylmorphinan, a d-isomer of the codeine analog, levorphanol. The inventive method has proven useful in controlling the progression of ALS in afflicted patients.

7 Claims, No Drawings

METHOD FOR TREATMENT OF AMYOTROPHIC LATERAL SCLEROSIS COMPRISING ADMINISTRATION OF DMP

This invention relates to a method for treatment of Amyotrophic Lateral Sclerosis and other neurodegenerative disorders. This invention further relates to a method for treatment of Amyotrophic Lateral Sclerosis and other neurodegenerative disorders by administering a medicament in controlled doses of therapeutically effective amounts.

BACKGROUND OF THE INVENTION

Amyotrophic Lateral Sclerosis (ALS) is a progressive degenerative disease of the motor system which is usually relentlessly progressive, leading to death in half the cases within three years of onset. It is related to a group of diverse motor-system diseases which include Huntington's Chorea, Parkinson's disease and Alzheimer's disease. Numerous agents have been tried therapeutically in ALS, but none have been unequivocally demonstrated to benefit the disorder.

ALS was once exceedingly common on the Marianas islands of Guam and Rota. The rates on these islands were as much as 100 times those for the United States. However, with Americanization of the population after World Was II, the incidence of ALS on these islands began to dramatically decline. This decline has been linked to the exclusion of the highly toxic seed of the false sago palm from the diet of the natives. It has subsequently been shown that an unusual nonprotein amino acid, beta-N-Methylamino-L-alanine or L-BMAA, present in the seed of the false sago plant, can produce an ALS-like motor disorder when fed to monkeys.

This suggested to us that the L-BMAA might be affecting a neuroreceptor type responsible for the ALS symptoms. It is known that other excitatory amino acids can bind in vitro to neuronal receptors. It has further been demonstrated in recent years that the dextrorotary opioid derivative dextromethorphan (DMP) binds to excitatory amino acid receptors in the brain. DMP has long been known as a highly effective cough suppressant. We, therefore, theorized that since a neuro-excitatory receptor in the brain appears to be adversely affected by L-BMAA and may produce the motor degeneration characteristic of ALS, the action of L-BMAA with the involved receptors might be antagonized by an agent such as DMP that suppresses central synaptic transmission.

SUMMARY OF THE INVENTION

It is thus one object of the invention to provide a method for treating ALS and other related disorders.

It is another object of the invention to provide a method for treating ALS and other related disorders by administering controlled doses of a medicament in amounts therapeutically effective for ALS and other related disorders.

Other objects, advantages, and novel features of the instant invention will be readily understood from the following descriptions and examples.

In accordance with the invention, a method is provided for treating ALS and other related disorders comprising providing therapeutically effective amounts of DMP or its salts, including DMP hydrobromide, on a regular and continuous basis. The DMP or its salts can be provided orally or rectally in doses in excess of those currently employed as an antitussive agent to provide protection from some types of exogenous and endogenous neuromotor toxins. The method of the instant invention can be useful in treating progressive motor system diseases such as ALS, and related disorders such as Huntington's Chorea, Parkinson's disease and Alzheimer's disease.

DETAILED DESCRIPTION OF THE INVENTION

In the practice of the invention, DMP is provided to the patient in dosages of from about 1.0 mg/kg per day to about 40 mg/kg per day as either a single prolonged release dosage or in two or more, preferably two to three, divided doses. In a preferred embodiment of the invention, DMP is provided to the patient in dosages of about 5.0 mg/kg per day to about 30 mg/kg per day, and in a most preferred embodiment of the invention, the dosage range is about 8.0–20 mg/kg per day. It is important to administer as high a dosage as is tolerable to the patient to maximize the therapeutic effect. The DMP should be administered on a regular and continuous basis. In some cases, it may be desireable to initiate low dosages of DMP and gradually increase the DMP dosage over time.

Suitable dosage forms will include a pharmaceutically acceptable vehicle for the DMP; the dosages may be administered in the form of pills, syrups, tablets, capsules, caplets and suspensions as well as suppositories for intrarectal administration.

Dextromethorphan is the sigma receptor agonist known as d-3-methoxy-N-methylmorphinan which is the d-isomer of the codeine analog, levorphanol. Dextromethorphan is commercially available from Sigma F & D Division, Ltd. Those skilled in the art of pharmaceutical preparation will recognize how to prepare the above-mentioned dosage forms of DMP as appropriate for use in the method of the instant invention.

The following examples illustrate the method of the instant invention as carried out in practical application. It is to be understood that these examples are for purposes of illustrations only and are not intended to limit the scope of the invention as set forth herein.

EXAMPLE 1

A fifty-one year old female suffering from ALS has been taking dextromethorphan for one year. Initially, she started at six tablespoons containing 270 mg (about 6 mg/kg) per day and is now at 12 tablespoons containing 540 mg (about 12 mg/kg) per day. Despite the progressive nature of this disease, her weight is 95 pounds and stable (her normal weight is 100 pounds). She is still able to walk and her fine motor skills have remained fair. Her arms are weak but she continues to be able to move without walkers, braces, or other aids. She has normal swallowing, breathing and speech function. It appears that the disease progression has stopped since she has been taking the medication.

EXAMPLE 2

Ten patients were entered into a double-blind, placebo-controlled trial of dextromethorphan in ALS. ALS was diagnosed if both upper and lower motor dysfunction were present as evidenced by muscular atrophy, fasciculations and weakness; and hyperreflexia, spasticity and long tract signs. The patients entered were 21 years of age or older and had weakness rated less than 5 and more than 3 on the Medical Royal College scale.

Patients did not have any of the following: significant concurrent disease; atypical symptoms that may involve secondary etiologies; any sensory abnormalities; cerebral involvement; neuro-ophthalmologoical signs; or excessive bulbar signs. No patient used any central nervous system depressants. Medication was dosed at 1.7 mg/kg in three divided doses per day. After two months of treatment, three patients are improved and two patients have stabilized.

Those skilled in the art will recognize that the instant invention encompasses those embodiments and modifications of the invention which do not constitute departures from the spirit and scope of the invention.

What is claimed is:

1. A method of treating a patient suffering from Amyotrophic Lateral Sclerosis, the method comprising administering controlled doses of DMP in a therapeutically effective amount in a pharmaceutically acceptable vehicle to said patient.

2. The method of claim 1 wherein the DMP and the pharmaceutically acceptable vehicle are in a dosage form selected from the group consisting of pills, syrups, tablets, capsules, caplets, suspensions, and intrarectal suppositories.

3. The method of claim 1 wherein the DMP is administered as a single prolonged release dosage per day.

4. The method of claim 1 wherein the DMP is administered as two or more divided doses per day.

5. The method of claim 1 wherein the DMP is administered in the amount of about 1.0–40 mg/kg per day.

6. The method of claim 5 wherein the DMP is administered in the amount of about 5.0–30 mg/kg per day.

7. The method of claim 6 wherein the DMP is administered in the amount of about 8.0–20 mg/kg per day.

* * * * *